United States Patent [19]

Cornue

[11] 4,050,456
[45] Sept. 27, 1977

[54] KNEE SPLINT

[76] Inventor: Robert L. Cornue, 3 Austin Road, Tully, N.Y. 13159

[21] Appl. No.: 597,514

[22] Filed: July 21, 1975

[51] Int. Cl.² .............................................. A61F 5/04
[52] U.S. Cl. .................................................... 128/88
[58] Field of Search ...................... 128/88, 87, 86, 85, 128/84, 83, 80

[56] References Cited

U.S. PATENT DOCUMENTS

| | | | |
|---|---|---|---|
| 1,334,596 | 3/1920 | Crouch | 128/85 |
| 1,961,118 | 5/1934 | Ettinger | 128/88 |
| 2,237,252 | 4/1941 | Longfellow | 128/87 R |
| 2,581,110 | 1/1952 | Kenworthy | 128/80 R X |

OTHER PUBLICATIONS

DePuy Combination Leg Splint, DePuy Fracture Appliance Catalogue, p. 31, copyright 1941.

Primary Examiner—John D. Yasko
Attorney, Agent, or Firm—D. Peter Hochberg

[57] ABSTRACT

An adjustable splint for a human knee comprising upper and lower leg engaging portions and a foot engaging portion. With a knee injury, it is important to splint the knee in the position in which it is found because changing the position can damage the blood vessels and nerves that pass through the knee. Therefore, the splint has hinged connections between its upper and lower leg engaging portions and between its lower leg and foot engaging portions so that its angular position can conform to that of the leg and foot. The upper and lower leg engaging portions of the splint each have a length adjustment, and the splint includes means for releasably securing its upper and lower portions in the required position of angular adjustment.

1 Claim, 3 Drawing Figures

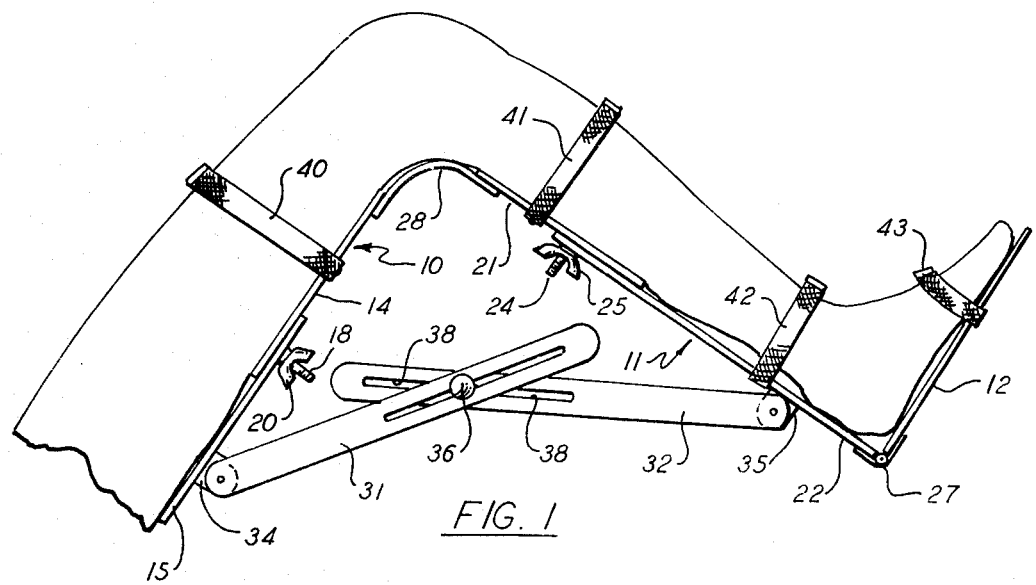
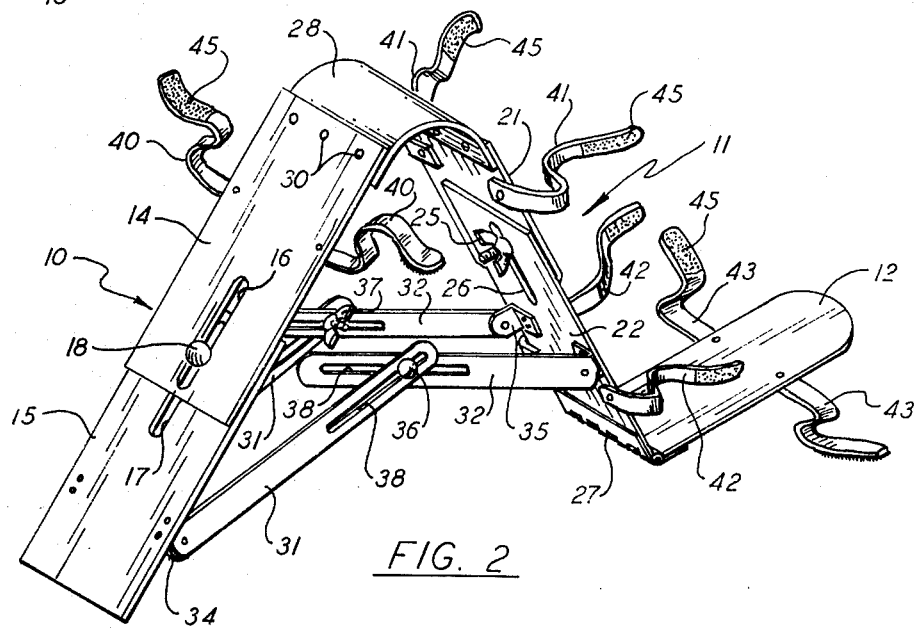
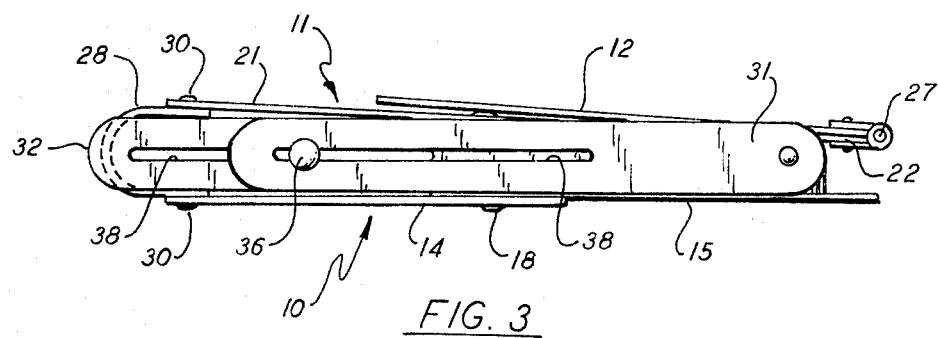

KNEE SPLINT

BACKGROUND OF THE INVENTION

This invention relates generally to surgical splints, and has particular reference to an improved hinged knee splint having angular and size adjustment means.

Many surgical splints have been developed heretofore including special splints for the knee. In emergency rescue and first aid treatment, when there is a knee injury it is important to splint the knee in the position in which it is found because changing the position can damage the blood vessels and nerves that pass through the knee. Since the leg having the injured knee may be bent to a greater or less degree, it is desirable that the knee splint be made up of sections that are hingedly connected together.

Hinged knee splints have been provided previously but of those known to the applicant most are for hospital use as where traction is necessary. As a result, these devices are usually relatively complex and not well suited for first aid or emergency rescue use. Splints of this type are disclosed in U.S. Pat Nos. 1,334,596; 3,651,803 and 3,762,405, and of these the first listed patent is the closest prior art known to the applicant.

SUMMARY OF THE INVENTION

The knee splint of the present invention is particularly well adapted for emergency rescue and first aid use in that it has a relatively simple yet completely adjustable structure. The splint is constructed so that it can be quickly and easily applied to the patient by one person, and thereafter it immobilizes the thigh and lower leg for subsequent handling of the patient. When not in use, the splint folds to a compact size for easy storage.

The knee splint includes upper and lower leg engaging portions and a foot engaging portion. The latter portion is hingedly connected to one end of the lower leg engaging portion, the other end of which is hingedly connected to one end of the upper leg engaging portion by a sheet or web of flexible material such a rubber. The hinged connections enable the angular configuration of the splint to conform to that of the patient's leg and foot, with the rubber hinge conforming comfortably with the contour of the back of the knee. The upper and lower leg engaging portions of the splint each have a length adjustment, and the splint includes means for releasably securing its upper and lower portions in the required position of angular adjustment.

BRIEF DESCRIPTION OF THE DRAWINGS

FIG. 1 is a side elevation of a knee splint embodying the invention, shown applied to the leg of a patient;

FIG. 2 is a perspective view of the splint in approximately the same position as in FIG. 1; and FIG. 3 is a side elevation of the splint in folded position.

DESCRIPTION OF THE PREFERRED EMBODIMENT

Having reference now to the drawings, the knee splint of the invention is essentially comprised of an upper leg engaging portion generally indicated at 10, a lower leg engaging portion generally indicated at 11 and a foot engaging portion 12. The upper leg engaging portion is comprised of two overlapping plates 14, 15 of a rigid lightweight material such as aluminum or plastic, and each of these plates has a longitudinally extending slot as best shown in FIG. 2. The slot 16 in the upper plate 14 is always at least partially in registry with the slot 17 in the lower plate 15 and a bolt 18 having a wing nut 20, FIG. 1, passes through the slots to connect the plates together. The overall length of the upper leg engaging portion 10 can be adjusted by varying the amount of overlap between plates 14 and 15 as will be apparent.

The lower leg engaging portion 11 has a construction similar to that of the upper leg engaging portion 10, the portion 11 being comprised of a pair of overlapping plates 21 and 22 adjustably connected together by a bolt 24 and a wing nut 25. The bolt passes through registering slots in the plates, only one of which slots is shown at 26 in FIG. 2. The foot engaging portion 12, which is also a plate of rigid lightweight material, is pivotally connected to plate 22 of the lower leg engaging portion as by a piano type hinge 27.

The upper and lower leg engaging portions 10 and 11 are pivotally connected together by a flexible sheet member 28, this member in the illustrated embodiment being a relatively thick sheet of rubber. The opposite ends of member 28 are secured to plates 14 and 21 of the upper and lower leg engaging portions respectively as by rivets 30. In addition to serving as a hinge, member 28 is dimensioned so that it spaces the ends of plates 14 and 21 apart whereby it can conform comfortably to the contour of the back of the knee as indicated in FIG. 1.

When the upper and lower leg engaging portions 10, 11 of the splint have been positioned so that their angular adjustment conforms to the position of the injured leg as shown in FIG. 1, they can be releasably secured in the adjusted position by two pairs of coacting elongated slide members 31 and 32. One end of each slide members 31 is pivotally connected to a bracket 34 riveted or otherwise secured to plate 15 of the upper leg engaging portion 10, the brackets being positioned adjacent opposite side edges of the plate as indicated. Similarly, one end of each slide members 32 is pivotally connected to a bracket 35 secured to plate 22 of the lower leg engaging portion 11, FIG. 2.

The free ends of the slide members 31, 32 on each side of the splint are in contact with one another and the contacting slide members are connected together by bolts 36 and wing nuts 37, the bolts passing through longitudinal slots 38 formed in each slide members. When the angular adjustment of the upper and lower leg engaging portions of the splint conforms to the leg, the normally loose wing nuts 37 are tightened to maintain the adjustment.

The knee splint is secured to the leg of the patient by a plurality of pairs of straps 40,41,42, and 43 respectively connected as by rivits to the plates 41,21,22 and 12. These straps are wrapped around the leg and the free ends of each pair are connected together by Velcro fasteners 45 or any other suitable fastening means. With the splint engaging only the bottom of the patient's leg, the top and sides thereof remain exposed enabling an attendant to watch for circulation, bleeding or other problems. In this connection, it should also be noted that the splint permits the leg to be X-rayed white it is still on the patient's leg.

FIG. 3 shows the splint in its compact folded position for ease in storage. When it is necessary to use the splint, it is opened out to a position as shown in FIG. 2 and then positioned under the patient's injured leg and the lengths of the upper and lower leg engaging portions 10 and 11 are adjusted to substantially conform to the patient's leg. Thereafter, the wing nuts 20 (which are normally loose in the folded, storage position of the splint) are tightened to maintain the length adjustments.

The straps 40,41,42 and 43 then are fastened around the leg. In this step, the hinged connections between the upper and lower leg engaging portions and the foot engaging portion permit the splint to conform to the angular position of the patient's leg and foot. Thereafter, the previously loose wing nuts 37 are tightened so that the slide members 31,32 maintain the angular adjustment between the upper and lower leg engaging portions, and the patient's knee is immobilized.

From the foregoing description it will be apparent that the invention provides an effective and efficient knee splint that is particularly well adapted for emergency rescue and first aid use. As will be apparent to those familiar with the art, the invention may be embodied in other specific forms without departing from the spirit or essential characteristics thereof.

I claim:

1. An adjustable knee splint including:
  an upper leg engaging portion comprising a first pair of overlapping rigid plate members, and means for adjusting the extent of overlap of said first pair of plate members to adjust the overall length of said upper leg engaging portion;
  a lower leg engaging portion comprising a second pair of overlapping rigid plate members and means for adjusting the extent of overlap of said second pair of plate members to adjust the overall length of said lower leg engaging portion;
  a foot engaging portion hingedly connected to one end of said lower leg engaging portion;
  a flexible, elastic sheet member connecting the other end of said lower leg engaging portion with one end of said upper leg engaging portion to separate the connected ends of said leg engaging portion, said sheet member having a non-metallic leg engaging surface;
  connecting means for interconnecting said upper and lower leg engaging portions, said connecting means comprising pairs of slide members, each pair of slide members including first and second elongated, longitudinally slotted overlapping slide members connected respectively at one end to said upper and lower leg engaging portions, and releasable fastening means extending through the slots of the respective pairs of slide members to interconnect the other ends of slide members, said other ends being connected only to each other;
  and straps connected to said upper and lower leg engaging portions and to said foot engaging portion, respectively, for securing a person's leg and foot to said splint.

* * * * *